United States Patent [19]

Mura

[11] Patent Number: 5,560,852
[45] Date of Patent: Oct. 1, 1996

[54] USE OF 4H-3,1-BENZOXAZIN-4-ONE COMPOUNDS TO IMPROVE THE LIGHT FASTNESS OF TEXTILE MATERIALS

[75] Inventor: Jean-Luc Mura, Rixheim, France

[73] Assignee: Sandoz Ltd., Basel, Switzerland

[21] Appl. No.: 408,507

[22] Filed: Mar. 22, 1995

[30] Foreign Application Priority Data

Mar. 26, 1994 [DE] Germany ............... 44 10 539.8

[51] Int. Cl.⁶ .................. D06M 13/355; C07D 265/00; C07D 273/00
[52] U.S. Cl. .................. 424/402; 544/92; 252/8.61; 252/380; 252/402; 252/403; 8/490
[58] Field of Search ............... 252/8.6, 8.8, 8.7, 252/8.75; 544/92

[56] References Cited

U.S. PATENT DOCUMENTS

| | | | |
|---|---|---|---|
| 3,408,326 | 10/1968 | Errede | 528/210 |
| 3,989,698 | 11/1976 | Jacobs et al. | 544/92 |
| 4,036,960 | 7/1977 | Chan | 424/248.5 |
| 4,446,262 | 5/1984 | Okumura et al. | 524/89 |
| 4,518,775 | 5/1985 | Allais et al. | 544/92 |

FOREIGN PATENT DOCUMENTS

| | | |
|---|---|---|
| A068327 | 1/1983 | European Pat. Off. |
| 490819 | 6/1992 | European Pat. Off. |
| 55-160025 | 3/1981 | Japan . |
| 59-12952 | 5/1984 | Japan . |
| 5-230346 | 9/1993 | Japan . |
| 1153994 | 6/1969 | United Kingdom . |

OTHER PUBLICATIONS

C.A. 120, 1994, 136958x, Abstract for JP 05, 195, 367, published Aug. 3, 1993.

English language translation, JP 05, 195367, published Aug. 3, 1993.

C.A. 120, 1994, 109408m, Abstract for JP 05, 230, 346, published Sep. 7, 1993.

English language translation, JP 05, 230, 346, published Sep. 7, 1993.

American Cyanamid technical sheet for CYGARD UV–3638 no date provided.

Modern Plastics Encyclopedia 92, pp. 192, 194, 196, 546, 547 no month provided.

*Primary Examiner*—Anthony Green
*Attorney, Agent, or Firm*—Robert S. Honor; Carl W. Battle; Hesna J. Pfeiffer

[57] ABSTRACT

A method of improving the light fastness of textile materials using an aqueous dispersion of a compound of formula I,

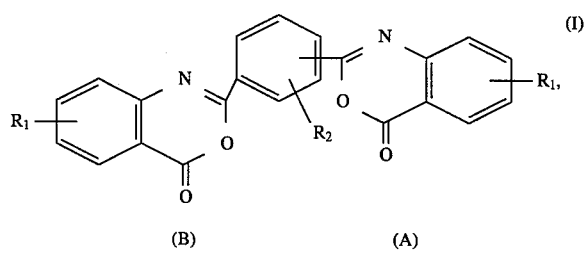

having a first (A) and a second (B) benzoxazine-4-one ring joined by a phenylene bridging member; a variable bond between the first benzoxazine-4-one ring (A) and the phenylene bridging member, said variable bond being meta- or para- to the bond between the second benzoxazine-4-one ring (B) and the bridging member; wherein each $R_1$ is independently hydrogen, halogen, nitro, $C_{1-2}$ alkyl, $C_{1-4}$ alkoxy, carboxy, sulfonic acid, $C_{1-3}$ alkylcarbonyl, benzoyl or $C_{1-4}$ alkoxycarbonyl and; $R_2$ is hydrogen, chlorine, bromine, methyl, $C_{1-2}$ alkoxy, phenyl, hydroxy, nitro, carboxy or sulfonic acid.

11 Claims, No Drawings

USE OF 4H-3,1-BENZOXAZIN-4-ONE COMPOUNDS TO IMPROVE THE LIGHT FASTNESS OF TEXTILE MATERIALS

The present invention relates to the use of 4H-3,1-benzoxazine-4-one compounds to improve the light fastness of textile material.

Such compounds are at least partially known from e.g. DE-OS 2556590, U.S. Pat. No. 3,408,326 and EP-A 0 068 327. From EP-A-0 068 327 it is known in particular that such compounds protect polymer compositions from ultraviolet light. EP-A-0 068 327 describes mainly the protection of various plastics articles, or transparent organic or inorganic materials used in applications which require shielding of ultraviolet light. Protection is acquired by incorporating the 4H-3,1-benzoxazine-4-one compound in an unreacted state into the polymer of a molded article or by first producing a molded article and then coating or impregnating it. For impregnation a solution of the 4H-3,1-benzoxazine-4-one compound in an organic solvent (e.g. ketones, esters, chlorinated carbohydrates and amides) is prepared and the polymer article is dipped in it, optionally under proper heating (p.20, second para.). Even though on p. 21, line 8 of EP-A-0 068 327 cloths are mentioned, nowhere else is there a reference to textiles, but mainly films, sheets or hollow articles such as tubes, pipes or containers are mentioned as polymer articles to be protected.

The problem of the present invention is to provide compounds in form of aqueous dispersions, which show excellent exhaustion and which are, therefore, suitable for impregnating textiles by exhaustion process or by a padding process.

This problem is solved by using an aqueous dispersion of one or several compounds of the general formula I

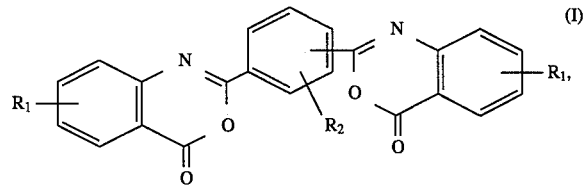

wherein
the variable bond between the one benzoxazine-4-one ring and the phenylene bridging member is in meta- or para-position to the bond of the other benzoxazine-4-one ring,
the two $R_1$ independently signify hydrogen, halogen, nitro, $C_{1-2}$alkyl, $C_{1-4}$alkoxy, carboxy, sulfonic acid, $C_{1-3}$alkylcarbonyl, benzoyl or $C_{1-4}$alkoxycarbonyl and
$R_2$ signifies a substituent selected from hydrogen, chlorine, bromine, methyl, $C_{1-2}$-alkoxy, phenyl, hydroxy, nitro, carboxy or sulfonic acid,
for improving the light fastness of textile materials.

The two $R_1$ preferably signify hydrogen, chlorine, bromine, methyl or $C_{1-2}$alkoxy, especially hydrogen.

$R_2$ preferably signifies hydrogen, chlorine, nitro or methyl, especially hydrogen.

The bonds of the benzoxazine-4-one rings to the phenylene bridge member are preferably in para-position.

In principle, all textile materials may be treated with the compounds of formula I.

These compounds are applied, during dyeing, in the same manner as dyestuffs which are appropriate for the corresponding textile material, preferably together with the dyestuffs. Thus, for fibres or filaments and the textiles produced therefrom, which consist of fully or semi-synthetic, hydrophobic, high molecular weight, organic matter, compounds of formula I which are free from water-solubilizing groups are used in finely-dispersed form. For textile materials consisting of natural or synthetic polyamides and cellulosic material (natural or regenerated), it is preferable to use acidic/anionic compounds of formula I.

The compounds of formula I may also be employed in a mixture with other UV-absorbers. Consequently the present invention also relates to mixtures in form of aqueous dispersions of compounds of formula I as defined above together with other UV-absorbers. Such other UV-absorbers are e.g. 2,4-dihydroxybenzophenone, 2,3,4-trihydroxy-benzophenone, 2-hydroxy- 4-methoxybenzophenone, 2,2',4,4'-tetrahydroxybenzophenone, 2,2'-dihydroxy-4,4'-dimethoxybenzophenone, 2-hydroxy-4-benzyloxybenzophenone, 2-(2H-benzotriazole-2-yl)- 4,6-bis(1-methyl-1-phenylethyl)phenole, 2-(2H-benzotriazole-2-yl)-4-(1,1,3,3-tetramethylbutyl)phenole, 2-(2H-benzotriazole-2-yl)-4-(1,1-dimethylethyl)-6-(1-methylpropyl)-phenole, 2-(2H-benzotriazole-2-yl)-4,6-bis(1-methylpropyl)phenole or 2-(2'-hydroxy-3'tert.butyl-5'methyl)-5-chlorobenzotriazole.

Production of the compounds of formula I is effected in the manner described in DE-OS 25 56 590 or U.S. Pat. No. 3,408,326.

As mentioned above, the compounds of formula I are applied to the various substrates in the same manner as the corresponding dyestuffs, e.g. from a so-called long or short aqueous bath, by the exhaust process or by a padding (slop-padding) process.

Fixing is similarly effected in the conventional manner for dyeing, during the exhaust treatment or by subsequent heating.

A great advantage of these compounds is their high fastness to sublimation. Also, the wet fastness, especially that of the compounds which are free from water-solubilizing groups, is very good. Also notable is the fact that the compounds of formula I do not have any intrinsic colour in the visible optical range.

The compounds of formula I are generally employed in quantities of 0.05 to 5, preferably 0.1 to 3, and especially 0.2 to 3%, based on the weight of the textile materials to be treated therewith.

The textiles treated according to the invention also very effectively screen those areas of skin of the wearer that are covered by the textiles against UV radiation from the sun.

In the following examples, the parts and percentages are by weight. One part by volume corresponds to the volume of one part by weight water (at +4° C.). The temperatures are given in degrees celsius.

EXAMPLE 1

163 parts of isatoic anhydride is introduced into 1500 parts of pyridine whilst stirring, under anhydrous conditions, heated to 60°, and mixed with 101.5 parts of terephthalic acid dichloride in portions, such that the temperature of the reaction mixture does not rise above 80°. The resultant carbon dioxide is drawn off. When the terephthalic acid dichloride addition is complete, the mixture is boiled for 4 hours under reflux cooling, then cooled to room temperature, the insoluble residue is filtered off, washed with methanol until free from chlorine, and dried.

The [2,2'-di-(4H-3,1-benzoxazin-4-one)]-p-phenylene thus obtained melts at 318°.

EXAMPLE 2

The process is effected as indicated in example 1, but instead of terephthalic acid dichloride, the same quantity of isophthalic acid dichloride is used, and one active substance is obtained, which has similar light-stabilizing activity to that of the compound obtained according to example 1.

EXAMPLE 3

5 parts of the compound obtained according to example 1 is ground for 3 hours in an appropriate dispersing apparatus with 2 parts of a dispersing agent based on oleyl alcohol/ethylene oxide (addition product), 83 parts of water and 150 parts of glass pearls. The average particle size of the active substance is then less than 5 μm, the glass pearls are separated from the dispersion using a sieve, and washed out with 10 parts of water. The dispersion obtained contains 5% active substance.

EXAMPLE 4

50 parts of a polyester-tricot material (commercial name "Tersuisse") is placed in 1000 parts of an aqueous liquor, which contains
0.8 pans of C.I. Disperse Yellow 42,
0.135 pans of C.I. Disperse Red 202,
0.135 pans of C.I. Disperse Red 86,
5.0 pans of the dispersion of example 3 and
2.0 pans of ammonium sulphate,
the pH value of the bath is adjusted to 4.5 in a HT dyeing apparatus, the material is treated for 5 minutes at 60°, then the bath is heated to 130° over ca. 30 minutes, and dyeing is effected at this temperature for 60 minutes. After cooling to 60°, the dyeing is removed from the bath, rinsed, cleaned for 20 minutes at 80° in the usual way with an alkaline solution of sodium hydrosulphite, rinsed with warm water, neutralized with acetic acid, centrifuged, and the remaining moisture dried in the air. Part of the dyeing is then additionally treated for 60 seconds at 210°.

A second dyeing is produced in the same way, but without the light stabiliser, and a example of each is exposed to light (in an Atlas equipment Ci35) in accordance with ISO 105-A02 "Grey Scale for Assessing Change in Colour". The light fastness (measured by the Minolta Chromameter 200) is as follows:

| number of exposure cycles | 2 cycles | treated for 60 secs., at 210° C. |
| --- | --- | --- |
| without UV absorber, marks | 2.5 | 2.4 |
| with UV absorber, marks | 3.5 | 3.4 |

(best mark = 5)

The results obtained indicate the good activity of the stabiliser used according to the invention, as well as its good fastness to sublimation.

EXAMPLE 5

15 pans of the compound obtained according to example 1 is mixed in an appropriate dispersing apparatus with 10 parts of 2-(2'-hydroxy-3'tert.butyl-5'methyl)-5-chlorobenzo-triazole, 15 pans of a commercial condensation product of ditolylethersulfonate and formaldehyde, 0.25 parts of a fungicide, 2 pans of a copolymer of ethylene oxide and propylene oxide and 57.75 parts of demineralized water and ground for about 4 hours with glass pearls in a pearl mill until the average particle size is less than 1 μm. The glass pearls are separated from the dispersion using a sieve.

EXAMPLE 6

50 pans of a polyester-tricot material (commercial name "Tersuisse") is placed in 1000 parts of an aqueous liquor, which contains
0.8 pans of C.I. Disperse Yellow 42,
0.135 parts of C.I. Disperse Red 202,
0.135 parts of C.I. Disperse Red 86,
1.0 parts of the dispersion of example 5 and
2.0 parts of ammonium sulphate,
the pH value of the bath is adjusted to 4.5 in a HT dyeing apparatus, the material is treated for 5 minutes at 60°, then the bath is heated to 130° over ca. 30 minutes and dyeing is effected at this temperature for 30 minutes. After cooling to 60°, the dyeing is removed from the bath, rinsed, cleaned under reducing conditions, neutralized and dried in the air. Part of the dyeing is then additionally fixed at different conditions.

A second dyeing is produced in the same way, but without the light stabiliser, and a sample of each is exposed to light in accordance with ISO 105-B06. The light fastness (measured by the Minolta Chromameter 200 "Grey Scale for Assessing Change in Colour") was as follows:

| | 2 cycles | | | |
| --- | --- | --- | --- | --- |
| Number of exposure cycles: | not fixed | 60 secs. 190° | 120 secs. 190° | 60 secs. 210° |
| without UV absorber, marks | 2.5 | 2.5 | 2.5 | 2.5 |
| with UV absorber, marks | 3.8 | 3.6 | 3.5 | 3.5 |

(best mark = 5)

The results obtained indicate the good activity of the mixture used according to the invention, as well as its good fastness to sublimation.

I claim:

1. The method of improving the light fastness of textile materials comprising impregnating a textile material with an aqueous dispersion of an effective amount to improve the light fastness of textile materials of a compound of formula I,

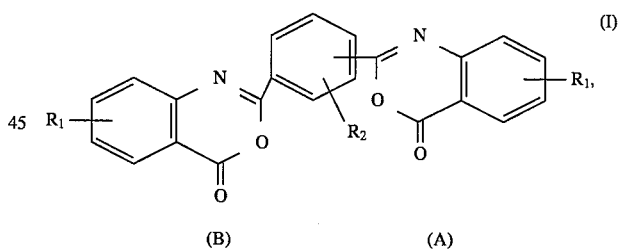

having a first (A) and a second (B) benzoxazine-4-one ring joined by a phenylene bridging member; a variable bond between the first benzoxazine-4-one ring (A) and the phenylene bridging member, said variable bond being meta- or para- to the bond between the second benzoxazine-4-one ring (B) and the bridging member; wherein each $R_1$ is independently hydrogen, halogen, nitro, $C_{1-2}$alkyl, $C_{1-4}$alkoxy, carboxy, sulfonic acid, $C_{1-3}$alkylcarbonyl, benzoyl or $C_{1-4}$alkoxycarbonyl and;

$R_2$ is hydrogen, chlorine, bromine, methyl, $C_{1-2}$alkoxy, phenyl, hydroxy, nitro, carboxy or sulfonic acid.

2. The method according to claim 1, wherein each $R_1$ is independently hydrogen, chlorine, bromine, methyl or $C_{1-2}$alkoxy.

3. The method according to claim 1, wherein each $R_1$ is hydrogen.

4. The method according to claim 1, wherein $R_2$ is hydrogen, chlorine, nitro or methyl.

5. The method according to claim 4, wherein $R_2$ is hydrogen.

6. The method according to claim 1, wherein the variable bond between the benzoxazin-4-one ring (A) and the phenylene bridging member is para to the position of the benzoxazine-4-one ring (B).

7. The method of claim 1, in which the aqueous dispersion contains 0.05 to 5% of the compound of Formula I, based on the weight of the textile material to be treated.

8. The textile material prepared by the method of claim 1.

9. The method of producing a textile which protects the wearer of said textile against UV rays from the sun comprising impregnating said textile with an aqueous dispersion of of a compound of formula I,

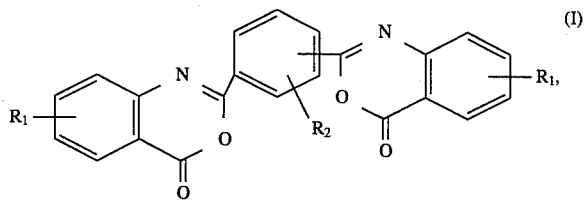

having a first (A) and a second (B) benzoxazine-4-one ring joined by a phenylene bridging member; a variable bond between the first benzoxazine-4-one ring (A) and the phenylene bridging member, said variable bond being meta- or para- to the bond between the second benzoxazine-4-one ring (B) and the bridging member; wherein each $R_1$ is independently hydrogen, halogen, nitro, $C_{1-2}$alkyl, $C_{1-4}$alkoxy, carboxy, sulfonic acid, $C_{1-3}$alkylcarbonyl, benzoyl or $C_{1-4}$alkoxycarbonyl and;

$R_2$ is hydrogen, chlorine, bromine, methyl, $C_{1-2}$alkoxy, phenyl, hydroxy, nitro, carboxy or sulfonic acid, said dispersion containing amount of the compound of formula I effective to protect the wearer of said textile against UV rays from the sun.

10. The method of claim 9 in which the aqueous dispersion contains 0.05 to 5% of the compound of formula I, based on the weight of the textile.

11. The textile prepared by the method of claim 10.

* * * * *